(12) United States Patent
Abrevaya et al.

(10) Patent No.: US 7,112,307 B2
(45) Date of Patent: Sep. 26, 2006

(54) RISER REACTOR SYSTEM FOR HYDROCARBON CRACKING

(75) Inventors: Hayim Abrevaya, Des Plaines, IL (US); Joel T. Walenga, Des Plaines, IL (US); Michael A. Schultz, Des Plaines, IL (US); Anil R. Oroskar, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 55 days.

(21) Appl. No.: 10/868,052

(22) Filed: Jun. 15, 2004

(65) Prior Publication Data

US 2004/0258580 A1    Dec. 23, 2004

Related U.S. Application Data

(62) Division of application No. 10/317,261, filed on Dec. 11, 2002, now Pat. No. 6,791,002.

(51) Int. Cl.
*B01J 8/26* (2006.01)
*B01J 8/12* (2006.01)

(52) U.S. Cl. ................ 422/142; 422/144; 422/145; 422/146; 422/147; 422/190; 422/214

(58) Field of Classification Search ............... 422/141, 422/142; 208/155, 156
See application file for complete search history.

(56) References Cited

U.S. PATENT DOCUMENTS

| | | | | |
|---|---|---|---|---|
| 2,325,611 A | * | 7/1943 | Keranen | 208/152 |
| 2,460,404 A | * | 2/1949 | Ward | 208/70 |
| 2,970,100 A | * | 1/1961 | Moritz | 208/65 |
| 3,347,778 A | * | 10/1967 | Dill et al. | 208/74 |
| 3,520,797 A | * | 7/1970 | Payne et al. | 208/72 |
| 4,966,681 A | * | 10/1990 | Herbst et al. | 208/74 |
| 5,506,365 A | | 4/1996 | Mauleon et al. | 585/329 |
| 5,965,012 A | | 10/1999 | Lomas | 208/113 |
| 6,339,181 B1 | | 1/2002 | Chen et al. | 585/653 |

FOREIGN PATENT DOCUMENTS

WO    WO 0185872 A2    11/2001

* cited by examiner

*Primary Examiner*—Alexa Doroshenk Neckel
*Assistant Examiner*—Jennifer A. Leung
(74) *Attorney, Agent, or Firm*—John G. Tolomei; Frank S. Molinaro; Arthur E. Gooding (57) ABSTRACT

A riser reactor system for conversion of hydrocarbon feedstock to ethylene and propylene is described. The riser reactor system prevents riser reactors with a plurality of inlet ports for feeding gases having different compositions and for controlling the residence time of a gas catalyst within the riser reactor.

3 Claims, 7 Drawing Sheets

RISER REACTOR SYSTEM FOR HYDROCARBON CRACKING

CROSS-REFERENCE TO RELATED APPLICATION

This application is a Division of application Ser. No. 10/317,261, filed Dec. 11, 2002, now U.S. Pat. No. 6,791, 002, the contents of which are hereby incorporated by reference.

FIELD OF THE INVENTION

This invention relates to a riser reactor system for producing ethylene and propylene from a hydrocarbon feed stream. The invention further relates to a device including multiple feed streams for enhancing ethylene and propylene production.

BACKGROUND OF THE INVENTION

Ethylene and propylene are light olefin hydrocarbons and are important chemicals for use in the production of other useful materials, such as polyethylene and polypropylene. Other materials that are important and produced from ethylene and propylene include vinyl chloride, ethylene oxide, ethylbenzene, and alcohol. Essentially all of ethylene and propylene is produced by steam cracking of pyrolysis of hydrocarbons. Hydrocarbons used as feedstock for light olefin production include natural gas, petroleum liquids, and carbonaceous materials including coal, recycled plastic or any organic material.

The amounts of ethylene and propylene produced are often limited by the process and the percentage of the ethylene and propylene produced is often fairly low. Factors affecting the conversion include residence time, temperature of the operation and composition of the feedstock. As the economy grows and expands, the demand for light olefins will increase. Because of the limited availability in the production of light olefins from current methods, new methods are desired for increasing yields from existing sources of hydrocarbons. In addition, new inventions to reactor designs can enhance light olefin production.

BRIEF SUMMARY OF THE INVENTION

The invention relates to a riser reactor system for the conversion of a hydrocarbon feedstock to ethylene and propylene. The riser reactor system includes at least one riser reactor unit with a plurality of inlet ports, a catalyst outlet port, and a gas outlet port. The gas-catalyst separation unit with an inlet port is in fluid communication with at least one riser reactor unit catalyst outlet port, and includes a gas outlet port and a catalyst outlet port. The riser reactor system also includes a catalyst regeneration unit with an inlet port in fluid communication with the catalyst outlet port of the gas-catalyst separation unit, and a catalyst outlet port in fluid communication with at least one of the inlet ports of the riser reactor unit. The invention provides for increased control and increased conversion of a hydrocarbon feedstock to ethylene and propylene.

In one embodiment, the riser reactor system includes a plurality of riser reactor units wherein each riser reactor unit has a catalyst inlet port, a gas inlet port, catalyst outlet ports and a gas outlet port. The system also includes a manifold having an inlet port and a plurality of outlet ports wherein the inlet port is in fluid communication with the catalyst regeneration unit outlet port and each riser reactor catalyst inlet port is in fluid communication with an outlet port of the manifold. The riser reactor system may further include a hydrocarbon separation unit having a gas inlet port in fluid communication with the plurality of riser reactor units gas outlet ports, and wherein a hydrocarbon separation unit separates ethylene and propylene from the hydrocarbon gas.

Optionally, the riser reactor system is a plurality of reactor units and may include the reactor units in a series wherein the gas outlet port from a reactor unit is in fluid communication with the gas inlet port of a successive reactor unit. The riser reactor system may further include at least one heat exchanger disposed between successive reactor units for further controlling the temperature of the gas entering a reactor unit. This provides control to prevent the gas temperature from rising to a level where unfavorable thermal cracking will occur.

Another embodiment of the present invention includes a countercurrent riser reactor system for selectively converting hydrocarbons to ethylene and propylene. The system includes a riser reactor unit with a plurality of inlet ports for admitting gas and catalyst to the unit, and a gas outlet port and a catalyst outlet port. The system further includes a gas-catalyst separation unit with an inlet port in fluid communication with the riser reactor catalyst outlet port. The system further includes a catalyst regeneration unit for regenerating catalyst to be fed to the riser reactor unit wherein the catalyst stream comprises catalyst particles sized to exceed the terminal velocity of the superficial gas velocity of the gas stream. An aspect of the countercurrent riser reactor system optionally may include a plurality of reactor units, and optionally may include heat exchanger units disposed between successive reactor units. This provides for additional control of the temperature of the gas to prevent the gas from reaching temperatures where unfavorable thermal cracking may occur.

Other objects, advantages and applications of the present invention will become apparent after a detailed description of the invention.

BRIEF DESCRIPTION OF THE DRAWINGS

The description herein makes reference to the accompanying drawings wherein like reference numerals refer to like parts throughout the several views and wherein.

DETAILED DESCRIPTION OF THE INVENTION

An improved riser reactor system is presented for converting crackable hydrocarbons selectively to ethylene and propylene. Use of catalysts provides for lowering the temperature and improving the amount of hydrocarbons converted to ethylene and propylene. Catalysts are favorable in that they provide for a conversion reaction or hydrocarbon cracking, at significantly lower temperatures. However, problems arise wherein as the reaction progresses, increased partial pressures of ethylene and propylene slow down the rate of reaction due to increased occupancy of ethylene and propylene on catalyst sites. This leads to longer residence time needed to increase the conversion rate. Longer residence times allows the hydrocarbon gases to heat up a greater amount. However, undesirable thermal cracking reactions take place as the gas heats up with a longer residence time. It is desirable to reduce the amount of undesirable products while trying to increase the amount of ethylene and propylene produced.

The reaction of a mixture of hydrocarbons to produce a selective and limited product stream requires considerable control. When optimizing production, control over temperatures and time can vary with differences in feedstock. In addition competing reactions can produce undesirable products, as well as products produced from earlier reactions can subsequently react reducing the desired products. An example illustrating the importance of reaction time on the general behavior of the reaction system is demonstrated by a simple model in FIGS. 1–3. For illustration purposes only the behavior is modeled as two parallel reactions and that the reactions are assumed to be first order and irreversible. The two sets of reactions are:

and

Figure 1:
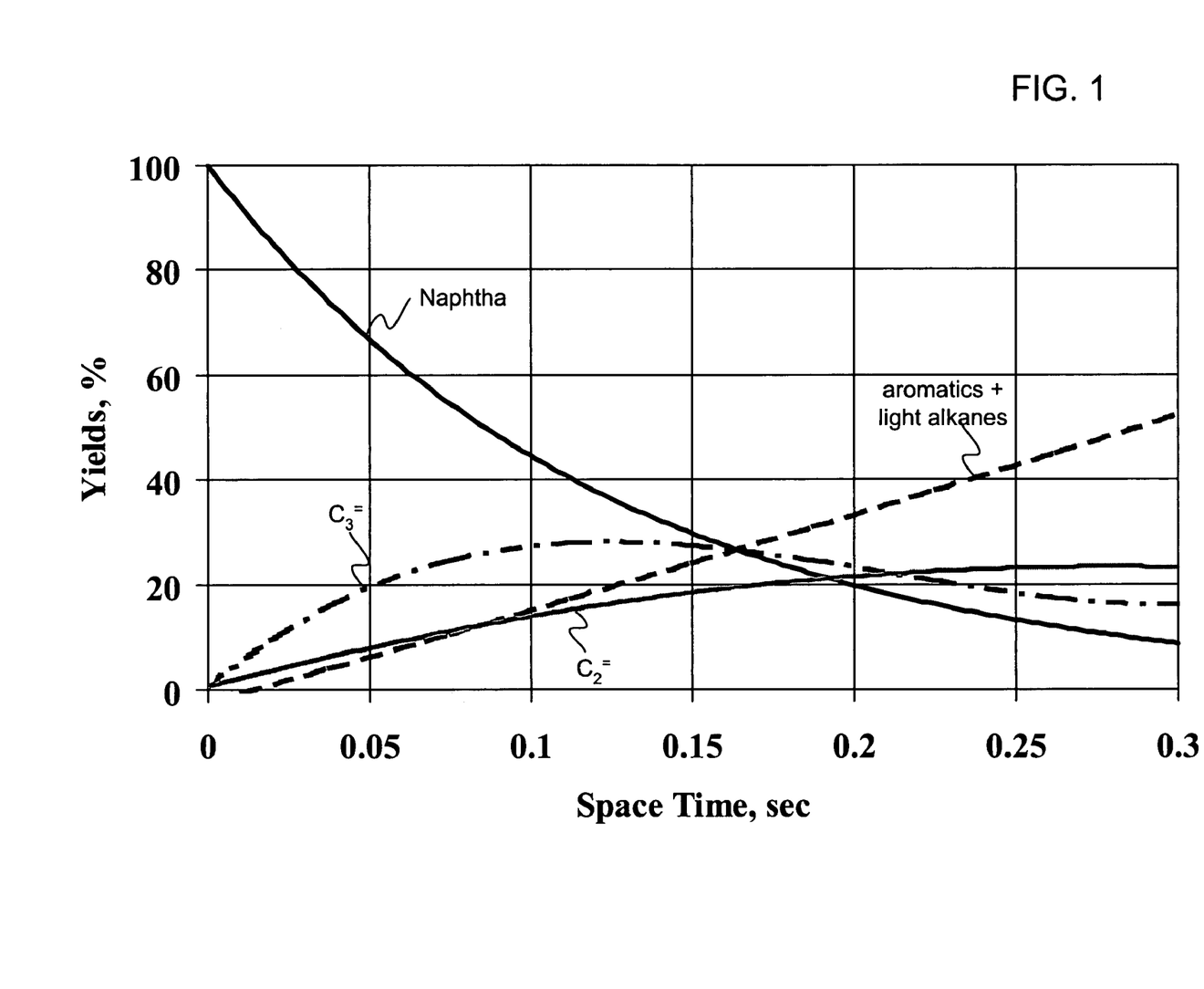
FIG. 1 is an illustration of a model reaction system.
Figure 2:
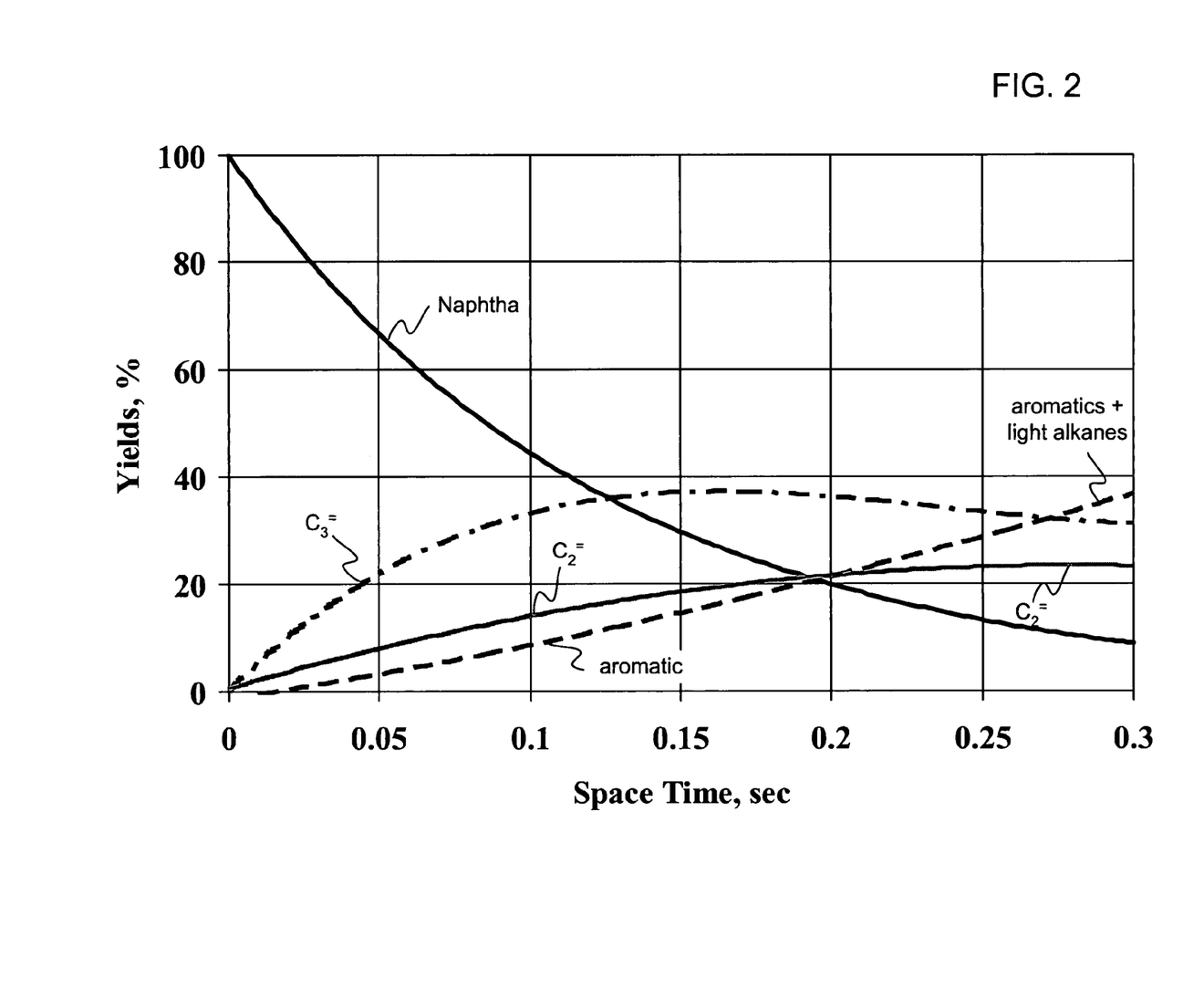
FIG. 2 is an illustration of the model reaction system with a reduced rate constant for conversion of propylene to aromatics.
Figure 3:
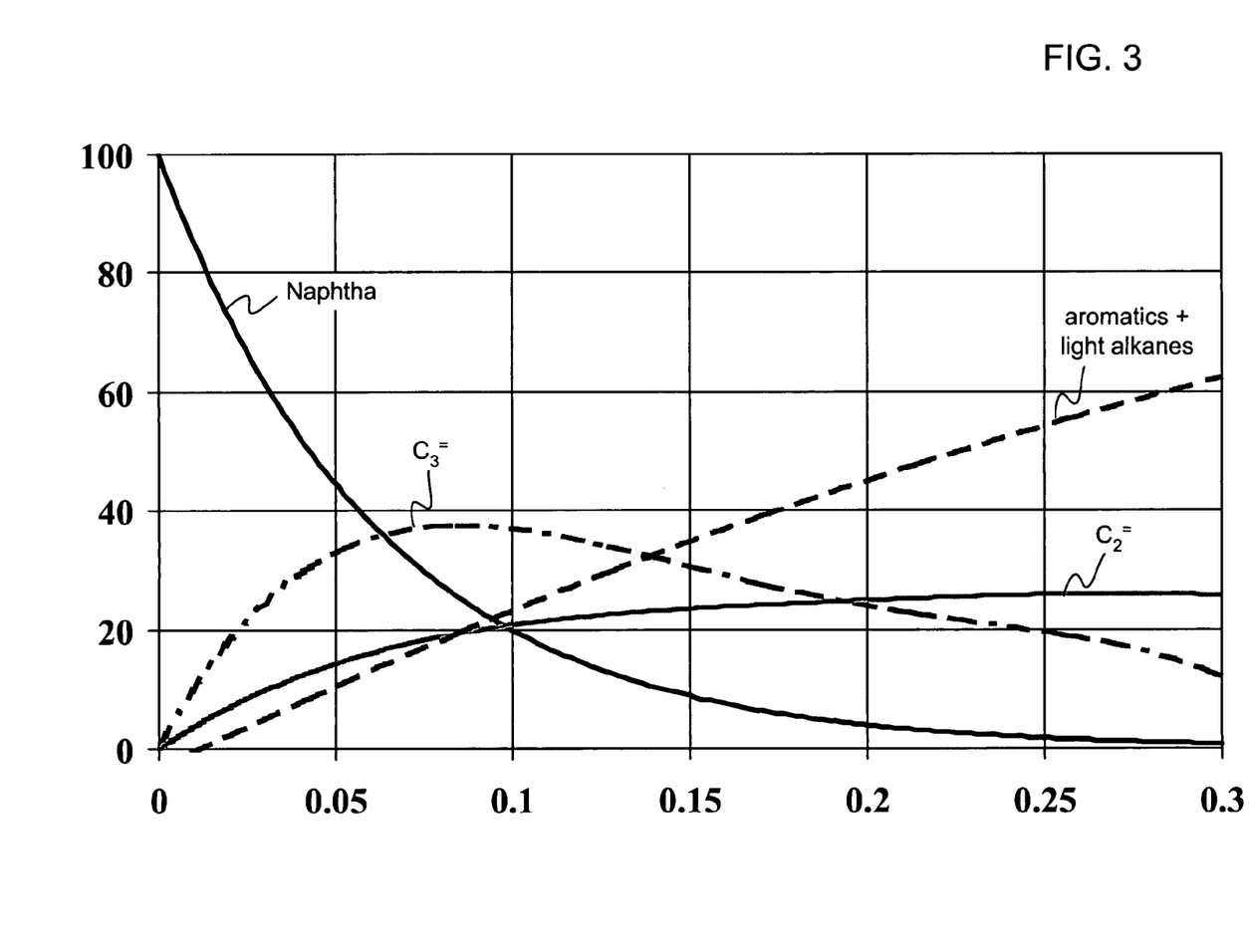
FIG. 3 is an illustration of the model reaction system with increased reaction rates for conversion of naphtha to olefins.

The reactions are parallel primary reactions for converting naphtha, A, to propylene, B and ethylene, D. Each time B and D are made, some light alkanes like methane and ethane are also produced. There is also a secondary reaction for converting propylene, B, to an aromatic product such as benzene, C, or to coke and light alkanes by hydrogen transfer.

FIG. 1 uses reaction constants of $k_1=6\text{sec}^{-1}$, $k_2=8\text{sec}^{-1}$ and $k_3=2.1\text{sec}^{-1}$. The model obtains yields and trends similar to those actually adsorbed in a pulse micro reactor and the range is 65–85% conversion. It can be seen through the model that extending the reaction time produces enhanced conversion to aromatics plus light alkanes and a reduction in valuable product yield. An optimal space time of about 0.15seconds achieves a maximum of B plus D, or propylene plus ethylene. FIG. 2 illustrates the same reaction system, with a reduced rate constant of $k_2=4\text{sec}^{-1}$ for the conversion of B to C, or reduced rate of propylene aromatization and hydrogen transfer. The rate constant was reduced by a factor of 2 and produced selectivity enhancement. This can be achieved through zeolite modification and has the impact of increasing the optimal space time for maximizing propylene plus ethylene (B plus D) production from about 0.15seconds to about 0.2seconds. FIG. 3 illustrates the same reaction system but with an increased rate constants for the primary reactions, $k_1$ and $k_3$ to $12\text{sec}^{-1}$ and $4.2\text{sec}^{-1}$ respectively. Increasing the rates of conversions for the primary reaction while maintaining the secondary reaction rate has the impact of reducing the optimal space to about 0.1seconds. Control of the production of desired light olefin products can be further achieved through the use of reactors adapted to control the contact times of the naphtha with the catalyst by limiting residence times. The results of which are demonstrated in specific embodiments detailed as follows.

Figure 4:
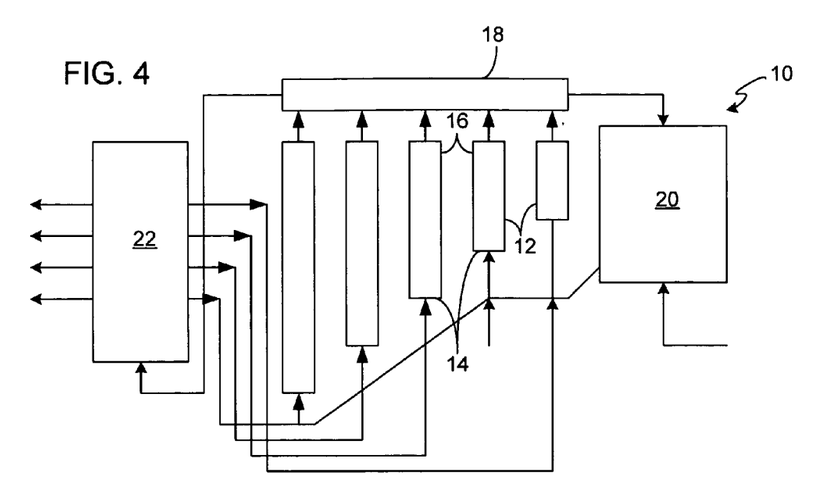
FIG. 4 is a schematic of the present invention including multiple reactor units.

FIG. 4 presents a first embodiment of the present invention. The riser reactor system includes in this embodiment a plurality of riser reactor unit 12. Each riser reactor unit 12 has an inlet port 14 and an outlet port 16. The inlet ports allow for the admission of gas reactants and the catalyst feeds, or as an alternative, the inlet ports 14 can be separate inlet ports for the gas and the catalyst. Outlet gas and catalysts exit the reactor through the outlet port 16 and then enter a gas-catalyst separation unit 18. The gas-catalyst separation unit 18 disengages the outlet gas from the catalyst and allows for the collection of the catalyst to be sent to catalyst regenerator 20. The disengaged outlet gas from the gas-catalyst separation unit is then directed to a hydrocarbon separation unit 22.

In an alternative to the gas-catalyst separation unit 18, each riser reactor unit 12 may include a gas catalyst separation zone (not shown). The catalyst would then be collected from the gas catalyst separation zone in a riser reactor unit 12 and directed to the catalyst regeneration unit 20, while the gas is directed to the hydrocarbon separation unit 22. The hydrocarbon separation unit 22 is any appropriate separation unit for purifying the desired product of ethylene and propylene from the outlet gas stream of the riser reactor units 12. In addition, the separation unit 22 can remove aromatics and methane to be redirected to other units or storage for other processes. In addition to separating out the desired products, separation units 22 can fractionate the remaining hydrocarbon stream into multiple recycle streams. Desired choices for recycle streams include an ethane stream, a propane-butane stream, a butene stream, and an aromatic-free $C_5^+$ recycle stream. Each of these streams is directed to a different riser reactor unit 12 as each stream requires different operating temperatures and residence times to produce optimal amounts of ethylene and propylene. Fresh naphtha can be fed to a separate riser reactor unit 12 or in an alternative, fresh naphtha can be processed through hydrocarbon separation unit 22 breaking the fresh naphtha into several streams to be fed with the recycle streams from the hydrocarbon separation unit 22.

One of the problems is that different hydrocarbons require different residence times and temperatures in order to achieve optimum conversion to ethylene and/or propylene. By providing a series of riser reactors units 12, individual control over feedstreams with different hydrocarbon compositions is obtained. The hydrocarbon separation unit 22 separates effluent hydrocarbon rich gas from at least one riser reactor unit 12 into a plurality of recycle streams. The recycle streams have different compositions and can be characterized by different molecular weights, by different boiling point ranges, or by the principal hydrocarbon constituents.

Figure 5:
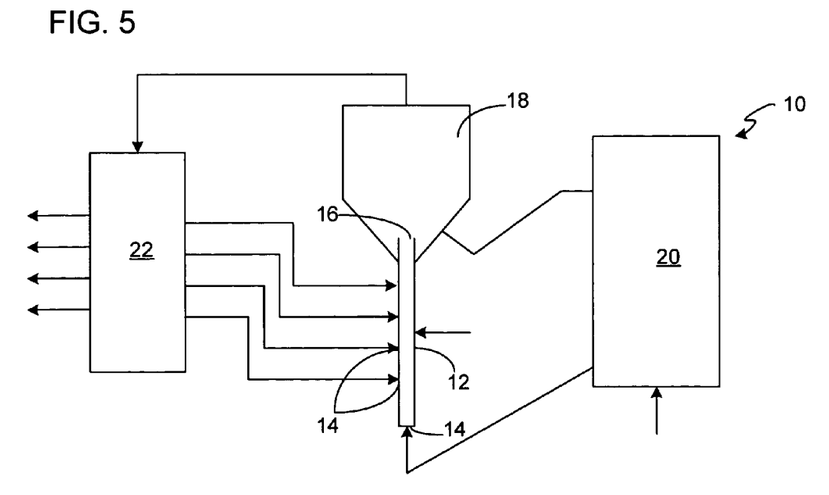
FIG. 5 is an alternate embodiment of the present invention including a single riser reactor with multiple hydrocarbon feed streams injected at different locations.

In a second embodiment of this invention, as shown in FIG. 5, the riser reactor system 10 includes a riser reactor unit 12 having multiple inlet ports for feeding in different feed streams having different hydrocarbon compositions. Multiple inlet ports provide control and allow for different streams to be input in different positions on a riser reactor and therefore allow for different residence times and/or operating conditions. The riser reactor unit 12 has an outlet port 16 which feeds the gas and catalyst into a gas catalyst disengagement unit 18 for separating the catalyst and riser reactor off-gas before further processing. In an alternative, the gas-catalyst separation unit 18 may be just a chamber on the end of the riser reactor unit 12. The used catalyst is directed to a catalyst regeneration unit 20. The catalyst regeneration unit 20 is any appropriate catalyst regeneration unit for regenerating the spent catalyst and recycling it back into the riser reactor unit 12. The product gas coming off of the gas-catalyst disengagement unit 18 is directed to a hydrocarbon separation unit 22. The hydrocarbon separation unit 22 provides for separating out the desired products of ethylene and propylene and directing the products downstream, as well as removal of undesirable constituents from the recycle stream such as methane and aromatics and directing the undesirable constituents for further processing or other storage.

The hydrocarbon separation unit 22 provides a plurality of recycle feed streams to be directed back to the riser reactor unit 12. The recycle streams include butene, an aromatics free $C_5^+$ liquid product, and one or more streams containing various amounts of propane, butane and ethane. The different feed streams are fed to the riser reactor unit 12 at different inlet ports 14 according to the desired residence time for the inlet constituents. The riser reactor unit 12, in addition, has an inlet port for fresh naphtha to be fed to the riser reactor unit 12. In an alternative, the fresh naphtha can be fed into the same inlet port as an aromatics free liquid product fed into the riser reactor unit 12. As an option, the riser reactor unit 12 may have different zones of operation wherein each zone can have separate temperature controls for the reaction taking place in each zone.

Figure 6:
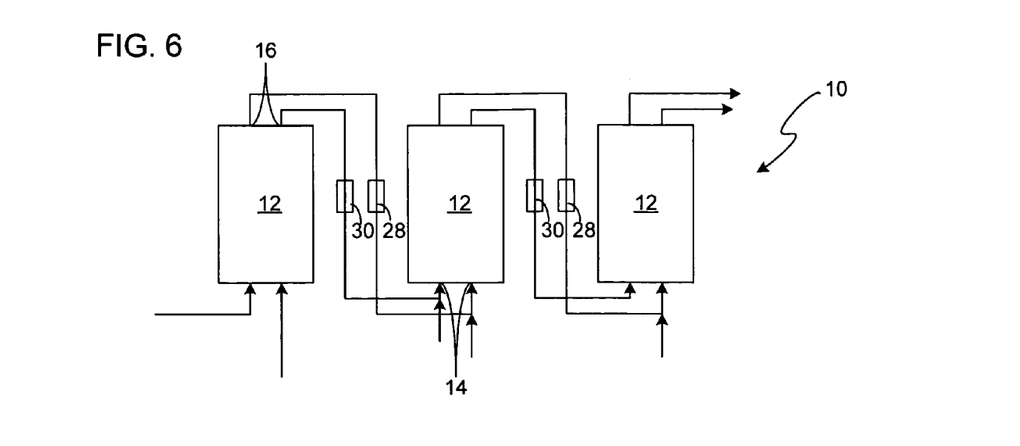
FIG. 6 is an alternate embodiment of the present invention entailing the use of reactor units in series and including heat exchangers between reactor units.

In another embodiment, as shown in FIG. 6, the riser reactor system 10 includes a plurality of riser reactor units 12 placed in a series configuration. A hydrocarbon feed gas and a catalyst are admitted to a first reactor unit 12 through inlet port 14. The catalyst and gas exit from the reactor unit 12 to outlet port 16 and are directed to the inlet port 14 of a second reactor unit 12. The catalyst and gas may be maintained as a single flow stream exiting one reactor unit 12 and fed into another reactor unit 12. In an alternative, the gas and catalyst are separated in a gas catalyst disengagement section of the riser reactor unit 12, and the gas catalyst disengagement section may be a separate unit attached to the outlet port 16 of the riser reactor unit. The use of a series of reactor units 12 provides for the addition of fresh catalyst to separate individual reactor unit 12 during the operation of the riser reactor system 10. The use of a series of riser reactor units also permits control of feeding different hydrocarbon feedstocks to the individual separate riser reactor units 12. This provides for controlling the reaction time and reaction conditions for different feedstocks fed to the riser reactor system 10, wherein feedstocks requiring longer reaction times are processed through multiple reactor units 12 while some feedstocks requiring short reactions times are processed through one or two reactor units 12. One aspect for improving ethylene and propylene production in a riser reactor system is controlling the temperature of the gas phase and temperatures of the catalyst in the system. It is desirable to have, before mixing, a relatively cold hydrocarbon feed stream and a relatively hot catalyst. An aspect of improving ethylene and propylene production is to reduce or prevent undesired thermal cracking reaction for the feed gas before it contacts the catalyst. A catalyst used in a riser reactor system can come from a catalyst regenerator at a very high temperature and be fed into the riser reactor system still exhibiting a temperature around 700° C. or greater. A hydrocarbon feedstock may be fed to a riser reactor system at a much cooler temperature of around 550° C. or lower. Upon contact of the gas and the catalyst, the gas can be expected to heat up and the catalyst expected to cool down. Allowing the gas to heat up a limited amount requires limiting the contact time between the gas and the catalyst. Depending on the particular feed stream, the total vapor contact time with the catalyst may be as short as 50–300 milliseconds.

The use of a series of riser reactor units permits more control over the contact time and temperature conditions of the reaction for producing ethylene and propylene. The use of multiple riser reactor units 12 permits the insertion of heat exchanger units between the riser reactor unit 12. In one embodiment, the gas product of a riser reactor unit 12 is fed through cooling heat exchanger unit 28 before being fed into a succeeding riser reactor unit 12. This enables sufficient control over the temperature of the gas to prevent the gas phase heating up to a range where undesirable thermal cracking might occur. The use of multiple riser reactor units also permits the insertion of heat exchanger 30 on the catalyst line to permit heating of the catalyst before reinsertion of the catalyst into a subsequent riser reactor unit 12.

Figure 7:
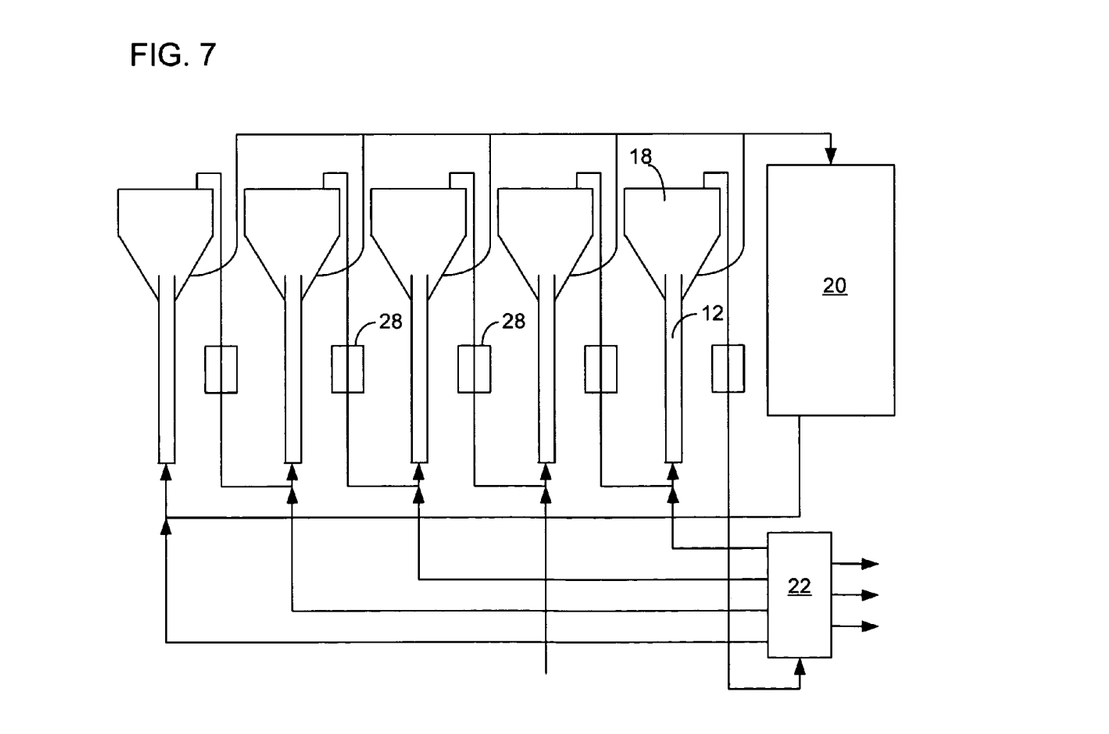
FIG. 7 is an alternate embodiment of the present invention including the use of multiple reactor units in series.

In an alternative embodiment, the invention comprises a series of riser reactor units 12. A series of riser reactor units 12 as shown in FIG. 7 include gas-catalyst disengagement chambers at the top of each riser reactor unit 12. The gas product coming out of the disengagement chamber 18 is then fed into a subsequent riser reactor unit 12 in series. The catalyst from each disengagement chamber 18 is directed to a regeneration unit 20. The regeneration unit 20 provides fresh catalyst feed into each of the riser reactor units 12. The product gas coming off the final riser reactor unit in a series is directed to hydrocarbon separation unit 22 wherein the gas is separated into a plurality of product streams and a plurality of recycle streams. The product streams include the desired ethylene and propylene streams as well as an aromatic stream and a methane stream. The aromatic and methane streams are removed as undesired feedstocks for ethylene and propylene production. The recycle streams, among which are included ethane and propane streams, butene streams, non-aromatic liquid streams, are then fed into different riser reactor units 12 depending on the desired residence time for each of the recycle feed streams. In addition, a fresh naphtha stream is fed into the appropriate riser reactor unit 12 according to the desired residence time for the naphtha stream. Optionally the reactor system 10 may include heat exchanger 28 between each successive pair of riser reactor units 12. This enables control of the gas inlet temperature to each of the riser reactor units 12. A catalyst fed to each of the riser reactor units can be controlled from the catalyst regeneration unit 20.

FIG. 7 presents a configuration for maintaining a substantial temperature difference between the catalyst temperature and the gas temperature. A hot catalyst coming from the catalyst regeneration unit 20 can be fed into the riser reactor unit 12 with a relatively cool gas. The relatively cool gas has a temperature significantly less than the catalyst temperature and the riser reactor unit 12 can be sized to limit the contact time between the gas and the catalyst to a duration less than the time needed to raise the gas temperature to a point where unfavorable cracking might occur. The amount of temperature rise in the gas will depend on the composition of the gas makeup. The riser reactor system 10 of the present invention can accommodate a variety of hydrocarbon vapor feeds in addition to a variety of hydrocarbon vapor streams coming from recycle streams of the hydrocarbon separator 22. Potential hydrocarbon feeds can include, but are not limited to, naphtha, gas oil, vacuum gas oil, Fischer-Tropsch black and mixtures thereof.

The riser reactor system 10 according to the present invention may also include a variety of catalysts used in each riser reactor unit 12. Among the catalysts available, although not limited to, include ferrierite, ZSM-5, erionite, ZSM-22, ZSM-23, ZSM-50, zeolite A, ZK-4, clinoptilolite, chabazite, Beta and Y- zeolite, wenkite, dachiardite, epistilbite, laumontite, wienebeneite, EU-1, ZSM-57, ZSM-11, NU-87, SUZ-4and mixtures thereof.

Figure 8:
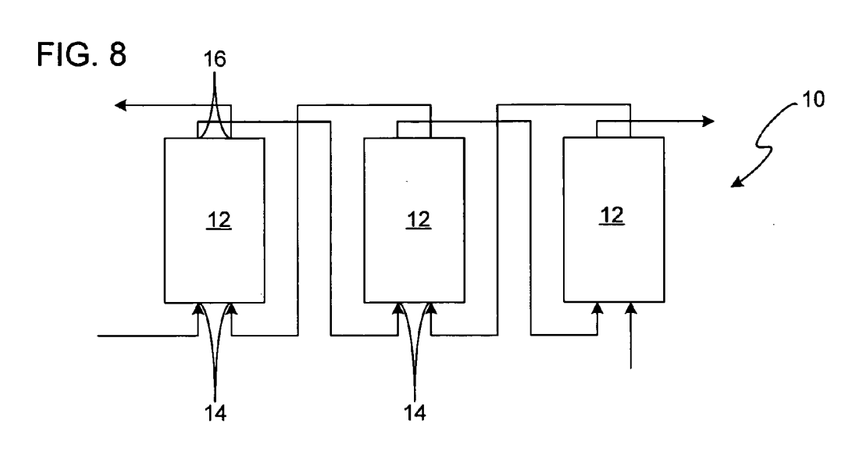
FIG. 8 is another alternate embodiment of the present invention.

In another embodiment of the present invention, as shown in FIG. 8, the riser reactor system 10 comprises a plurality of riser reactor units 12. Riser reactor units 12 are arrayed in series formation. In each riser reactor unit 12 the catalyst and gas flow in a co-current manner. However, the flow between the reactor units 12 is in a countercurrent manner for the gas and the catalyst. The catalyst enters a first reactor unit 12 through an inlet port 14, flows out of the first reactor unit 12 and outlet port 16. The catalyst is then fed into a subsequent reactor unit 12 wherein the catalyst flows through the reactor, out of the reactor, and is fed to another subsequent reactor until the catalyst reaches the final reactor in the series. The catalyst is then sent to a catalyst regeneration unit 20. The hydrocarbon gas is fed into an inlet port 14 of the last riser reactor unit 12. The gas coming off the last riser reactor unit 12 is then fed into an inlet port 14 of the preceding riser reactor unit 12. This continues until the off gas of a riser reactor unit is fed into the inlet port 14 of the first riser reactor unit 12 in the series. The off gas of the first riser reactor unit 12 is directed to a hydrocarbon separation unit 22. Alternate embodiments may include heat exchangers between successive riser reactor units 12.

Figure 9:
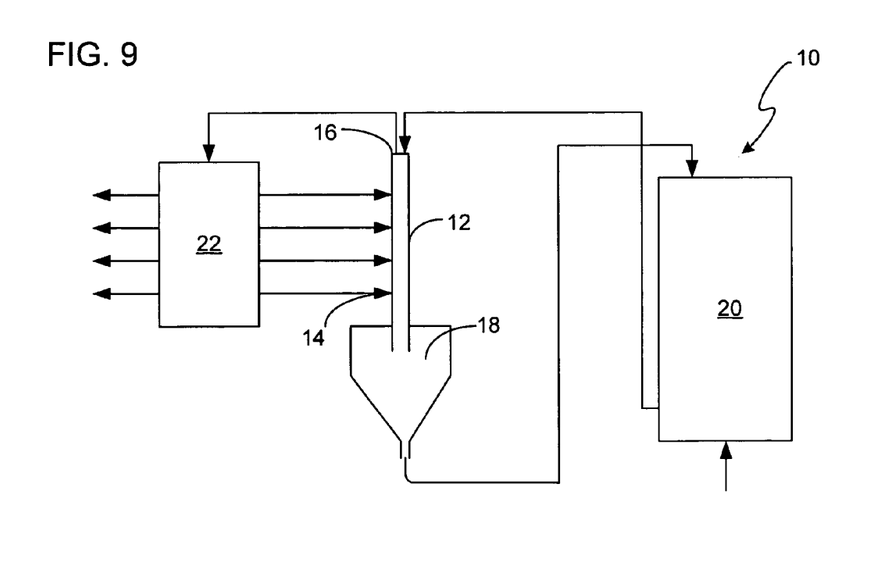
FIG. 9 is an embodiment of the present invention using a countercurrent flow reactor with multiple feed streams.

An alternate embodiment of the present invention includes a countercurrent riser reactor system for selectively converting hydrocarbons to ethylene and propylene. As shown in FIG. 9, a countercurrent riser reactor system 10 includes at least one riser reactor unit 12. The riser reactor unit 12 includes a plurality of inlet ports 14 for admitting gases having different compositions at different inlet ports along the riser reactor unit 12. The different inlet ports 14 along the riser reactor unit 12 may be at intermediate positions between different stages in the riser reactor unit 12. A catalyst is fed into the riser reactor unit 12 at the top of the riser reactor unit 12 wherein the catalyst falls in a countercurrent direction to the gases admitted to the riser reactor unit 12. The catalyst upon exiting the riser reactor unit 12 enters into a gas catalyst disengagement chamber 18 wherein the catalyst separates from the gas and the gas is allowed to rise in the riser reactor unit 12. A gas stream exits the riser reactor unit 12 at an exit port 16 at the top of the riser reactor unit 12. Optionally a gas catalyst disengagement unit 18 (not shown) may also be included at the top of the riser reactor unit 12 to collect any small amounts of catalyst that may be entrained with the gas exiting the riser reactor unit 12. The gas from the riser reactor unit 12 is directed to a hydrocarbon separation unit 22 for separating out the desired product of ethylene and propylene, as well as undesired reactant materials such as methane and/or aromatics. Other components such as ethane, butane, propane and non-aromatics naphtha liquid are directed back as recycle product stream into the riser reactor unit 12. Catalyst collected from the catalyst separation unit 18 is directed to a catalyst regeneration unit 20 wherein the catalyst is regenerated and subsequently sent back into the top of the riser reactor unit 12. A fresh naphtha stream may be fed directly into the riser reactor unit 12, or in an alternative, a fresh naphtha stream may be fractionated to streams having different compositions and then fed in different stages in the riser reactor unit 12. One aspect of this embodiment allows for control over the contact time permitted between different gas streams and the catalyst for converting the hydrocarbon feed stream to ethylene and propylene. Optional variations on this embodiment include a plurality of riser reactor units wherein the gas stream and the catalyst stream are fed from the outlet of one riser reactor unit 12 to the inlet of a successive riser reactor unit 12. In addition, heat exchanger units may be added between different stages in the riser reactor unit 12 to help keep the gas below a specified temperature, or to heat up the catalyst to a specified temperature.

Figure 10:
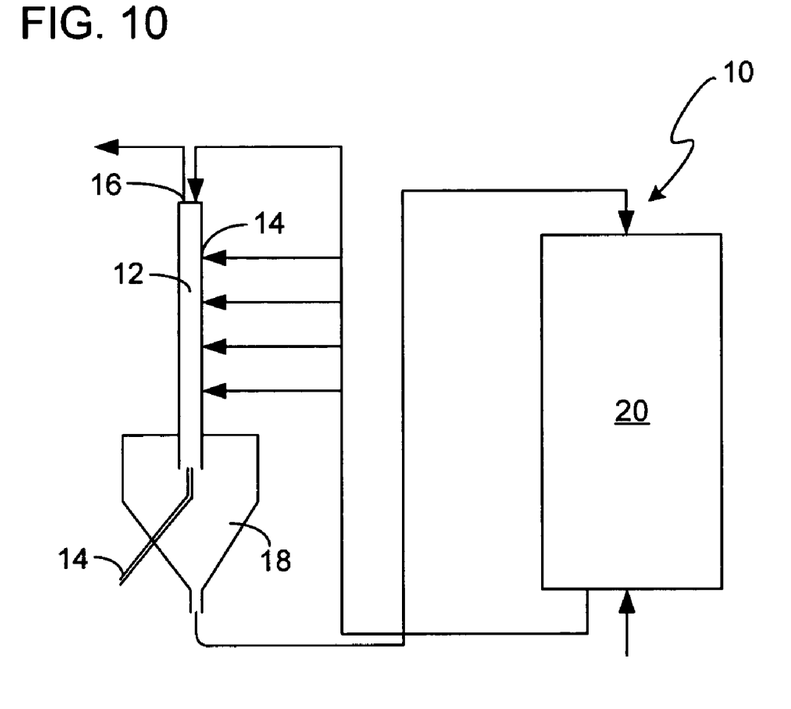
FIG. 10 is an alternate embodiment of a countercurrent flow reactor of the present invention using multiple catalyst feed streams.

Another embodiment of a countercurrent riser reactor system of the present invention is shown in FIG. 10. In this embodiment, the riser reactor includes a plurality of inlet ports 14 for admitting catalyst at different sections of the riser reactor unit 12. The inlet ports deliver fresh catalyst from the catalyst regeneration unit 20. This configuration provides for fresh catalyst contacting a gas having increasing concentrations of ethylene and propylene. The fresh catalyst helps overcome the problems with increased partial pressures of the ethylene and propylene gases affecting the rate of reactions.

In this configuration, hydrocarbon gas is admitted to an inlet port at the bottom of the riser reactor unit 12 and rises in a countercurrent flow to the catalyst admitted at plurality of inlet ports 14 along the height of the riser reactor unit 12. The catalyst flows out of the riser reactor unit 12 and into a gas catalyst disengagement chamber 18 where the catalyst is collected and directed to the catalyst regeneration unit 20. The feed gas includes fresh hydrocarbon gas, and optional recycle hydrocarbon gases and enters the riser reactor unit 12 and exits an outlet port 16 at the top of the riser reactor unit 12. A product gas of the riser reactor unit 12 is subsequently directed to separate out desired products of ethylene and propylene from the remaining constituents of the product gas. Alternate configurations of this embodiment include a plurality of riser reactor subunits where a subunit has a gas inlet port, at least one catalyst inlet port, a gas outlet port and a catalyst outlet port. This alternate embodiment with a plurality of reactor subunits provides for a series of reactors for treatment of the gas wherein the gas from a preceding reactor is fed to the inlet gas port of a succeeding reactor subunit. Alternate embodiments further provide for the use of heat exchanger units disposed between successive reactor subunits.

In operation of the multiple riser reactor units for cracking hydrocarbons, a feed stream of naphtha in a gaseous phase is fed into a riser reactor unit. A separate feed stream of catalyst is also fed into the riser reactor. The riser reactor unit produces an effluent stream which includes the catalyst and a gas phase comprised of methane, ethylene, propylene, ethane, propane, butanes, butenes, and higher molecular weight hydrocarbons. The catalyst is separated from the effluent stream and directed to a catalyst regeneration unit. The gas phase is directed to a hydrocarbon gas phase separation unit.

The hydrocarbon gas phase separation unit separates the gas phase in to product streams of ethylene and propylene, effluent streams of methane and aromatics, and recycle streams of ethane, propane and butanes, butenes, and an aromatics free stream containing $C_5^+$ hydrocarbons. The recycle streams are directed to different individual riser reactor units, with the ethane stream directed to a first riser reactor unit, the propane and butane stream directed to a second riser reactor unit, the aromatics free stream to a third riser reactor unit, and the butenes directed to a fourth riser reactor unit. The naphtha feed is directed to a fifth riser reactor unit.

The riser reactor units are operated at temperatures from about 500° C. to about 800° C. The residence times for contacting the hydrocarbons with the catalyst range from about 25 msec to about 600 msec. Preferably the operating conditions are a temperature from about 600° C. to about 700° C., with residence times from about 50msec to about 300msec.

The operating conditions vary for the different reactors based upon the feed. The times and temperatures depend on the reactivity of the hydrocarbons with the least reactive requiring longer residence times and higher temperatures, and the most reactive requiring shorter residence times and lower temperatures. Ethane the least reactive hydrocarbon will require higher operating temperatures and longer residence times. The propane/butane stream, the aromatics free naphtha stream, and the butene stream will require progressively lower operating temperatures and shorter residence times, with the butene stream having the lowest operating temperature and the shortest residence time.

The residence time can also be adjusted with the amount of coking on the catalyst, with increased coking allowing for longer residence times. A preferred amount of coking is from about 0.01 to about 1 weight percent carbon on the catalyst.

While the operation was given for a series of riser reactors, each with a different feed gas, the operation is similar for a single riser reactor with multiple inlet ports. The multiple inlet ports provide for injecting different feed gases at different positions in the riser reactor, thereby controlling the residence times and operating conditions of the different feed gases.

A series of tests were conducted using a pulse micro reactor to determine operating conditions of the riser reactor units. Naphtha is a complex mixture of hydrocarbons including predominantly normal alkanes, iso-alkanes, and naphthenes. A first series of tests were performed on using various model feeds made predominantly of single components found in naphtha, and likely to be present in a typical crackable hydrocarbon feedstock. The model feed compounds used for the first series of tests were n-heptane, i-pentane, n-pentane, 2-methyl pentane, 2,2-dimethyl butane, n-hexane, cyclohexane, and cyclopentane. The microreactors were operated at 550° C. and loaded with 0.4gm of ferrierite zeolite. The ferrierite had a relatively low silica to alumina ratio of 17. A 50microliter vapor feed pulse of hydrocarbon was injected into the microreactor with a 30scc/min helium carrier gas flow. The results are summarized in Table 1, which shows the conversion and average selectivities of the various feeds. Ferrierite, in general, shows a high selectivity for ethylene and propylene using various feeds. The most reactive was the n-heptane with n-hexane and n-pentane having slightly lower reactivities. The branched alkanes as feed showed higher selectivities for methane, and the naphthenes showed higher selectivity for aromatics. The naphthenes also had the lowest reactivities, especially cyclohexane. Cyclohexane's low reactivity is partly due to its relatively large kinetic diameter of about 6Å.

TABLE 1

| Feed | n-heptane | i-pentane | n-pentane | 2-methyl pentane |
|---|---|---|---|---|
| Selectivities, % | | | | |
| Methane | 6.8 | 12.3 | 6.8 | 11.4 |
| Ethylene | 27.9 | 34.9 | 26.1 | 27.4 |
| Ethane | 11.6 | 3.4 | 22.2 | 2.5 |
| Propylene | 24.4 | 26.4 | 22.7 | 31.4 |
| Propane | 7.5 | 3.2 | 4.9 | 4.5 |
| Butanes | 3.3 | 8.0 | 6.1 | 5.6 |
| Butenes | 4.5 | 4.5 | 2.7 | 3.0 |
| $C_5$–$C_7$ olefins | 5.6 | 2.3 | 1.6 | 6.7 |
| >$C_7$ olefins | 2.3 | 1.6 | 1.9 | 1.8 |
| Aromatics | 6.1 | 3.4 | 5.0 | 5.7 |
| Total | 100 | 100 | 100 | 100 |
| Conversion, % | 98.3 | 77.7 | 96.2 | 90.8 |

| Feed | 2,2 dimethyl butane | n-hexane | Cyclohexane | Cyclopentane |
|---|---|---|---|---|
| Selectivities, % | | | | |
| Methane | 18.5 | 7.7 | 4.3 | 5.5 |
| Ethylene | 30.8 | 27.5 | 22.0 | 31.0 |
| Ethane | 2.4 | 14.4 | 1.4 | 2.3 |
| Propylene | 26.5 | 25.3 | 20.7 | 29.4 |
| Propane | 2.4 | 7.9 | 6.1 | 4.1 |
| Butanes | 2.3 | 2.3 | 4.2 | 1.6 |
| Butenes | 3.5 | 3.0 | 2.0 | 1.8 |
| $C_5$–$C_7$ olefins | 4.5 | 3.4 | 6.3 | 9.7 |
| >$C_7$ olefins | 2.1 | 1.9 | 8.1 | 5.3 |
| Aromatics | 7.0 | 6.6 | 24.9 | 9.3 |
| Total | 100 | 100 | 100 | 100 |
| Conversion, % | 89.3 | 97.1 | 60.2 | 64.7 |

A further series of tests were conducted using light alkanes and 1-butene for feeds. The feeds for the lighter alkanes were ethane, propane, butane, and 1-butene. The results indicate that over ferrierite very high selectivities are obtained for ethylene. The microreactors were operated at 650° C. and loaded with 0.1 gm of ferrierite zeolite. The ferrierite was the same ferrierite as used above. A 50 microliter vapor feed pulse of hydrocarbon was injected into the microreactor with a 30 scc/min helium carrier gas flow. The results are summarized in Table 2 and show the selectivities from the different feeds. Ethane had the lowest reactivity, and for the lighter alkane feeds, the major products were ethylene and methane. However, for the propane, n-butane, and 1-butene feeds significant amounts of propylene was formed.

While ethane showed a much lower conversion at 650° C. than either propane or butane, test runs with an ethane feed at 700° C. and 750° C. showed increases in rates of conversion of 12% and 27% respectively, indicating that improved results are obtained by different operating conditions for different feeds.

TABLE 2

| Feed | ethane | propane | n-butane | 1-butene |
|---|---|---|---|---|
| Selectivities, % | | | | |
| Methane | 7 | 30 | 19 | 13 |
| Ethylene | 88 | 36 | 33 | 49 |
| Ethane | 0 | 3 | 14 | 4 |
| Propylene | 4 | 16 | 16 | 12 |

TABLE 2-continued

| Feed | ethane | propane | n-butane | 1-butene |
|---|---|---|---|---|
| Propane | 1 | 0 | 1 | 1 |
| Butenes | 0 | 3 | 3 | 0 |
| Aromatics | 0 | 10 | 12 | 19 |
| Others | 0 | 2 | 2 | 2 |
| Total | 100 | 100 | 100 | 100 |
| Conversion, % | 8 | 98 | 97 | 98 |

While the invention has been described in connection with what is presently considered to be the most practical preferred embodiment, it is to be understood that the invention is not to be limited to the disclosed embodiment but, on the contrary, is intended to cover various modifications and equivalent arrangements included with the spirit and scope of the appended claims, which scope is to be accorded the broadest interpretation so as to encompass all such modifications and equivalent structures as is permitted under the law.

What is claimed is:

1. A riser reactor apparatus for the conversion of a hydrocarbon feedstock to a hydrocarbon gas comprising ethylene and propylene comprising:
a plurality of riser reactor units wherein each riser reactor unit includes a plurality of sections, a catalyst inlet port, a plurality of gas inlet ports and a gas-catalyst outlet port, and wherein each gas inlet port enters at a different section of the riser reactor unit, and wherein the plurality of riser reactor units are arranged in series such that the gas-catalyst outlet port of a preceding reactor unit is in fluid communication with the catalyst and gas inlet ports of a successive reactor unit;
a plurality of gas-catalyst separation units, each separation unit with an inlet port in fluid communication with each riser reactor unit gas-catalyst outlet port, each separation unit further comprising a gas outlet port and a catalyst outlet port;
a catalyst regeneration unit with an inlet port in fluid communication with the catalyst outlet port of at least one of said gas-catalyst separation units, and a catalyst outlet port in fluid communication with the catalyst inlet port of at least one of said riser reactor units;
a manifold having an inlet port and a plurality of outlet ports, wherein the manifold inlet port is in fluid communication with the catalyst regeneration unit catalyst outlet port, and each riser reactor unit catalyst inlet port is in fluid communication with one of said outlet ports of the manifold;
a hydrocarbon separation unit having a gas inlet port in fluid communication with the gas-catalyst separation unit gas outlet ports, wherein the hydrocarbon separation unit separates ethylene and propylene from the hydrocarbon gas; and
at least one heat exchanger disposed between the gas-catalyst separation unit of a preceding reactor unit and a successive reactor unit for changing the temperature of the catalyst from the preceding reactor unit before directing the catalyst to the successive reactor unit, wherein said at least one heat exchanger comprises an inlet port in fluid communication with the gas-catalyst separation unit catalyst outlet port of the preceding reactor unit and an outlet port in fluid communication with the successive reactor unit catalyst inlet port.

2. A riser reactor apparatus for the conversion of a hydrocarbon feedstock to a hydrocarbon gas comprising ethylene and propylene comprising:
a plurality of riser reactor units wherein each reactor unit has at least one gas inlet port, a catalyst inlet port, and a gas-catalyst outlet port, wherein the plurality of riser reactor units are arranged in series such that the gas-catalyst outlet port of a preceding reactor unit is in fluid communication with the catalyst and gas inlet ports of a successive reactor unit;
a plurality of gas-catalyst separation units, each separation unit with an inlet port in fluid communication with each riser reactor unit gas-catalyst outlet port, each separation unit further comprising a gas outlet port and a catalyst outlet port;
a catalyst regeneration unit with an inlet port in fluid communication with the catalyst outlet port of at least one of the gas-catalyst separation units, and a catalyst outlet port in fluid communication with the catalyst inlet port of at least one of the riser reactor units;
wherein the catalyst inlet port of each riser reactor unit is located at the top of the riser reactor unit, and the catalyst regeneration unit catalyst outlet port is in fluid communication with the riser reactor unit catalyst inlet port, wherein a catalyst stream flows from the catalyst regeneration unit to the riser reactor unit and the catalyst stream is comprised of catalyst particles sized such that the terminal velocity of the catalyst particles is greater than the superficial velocity of the gas in the riser reactor unit, producing a counter current flow of catalyst particles;
a manifold having an inlet port and a plurality of outlet ports, wherein the manifold inlet port is in fluid communication With the catalyst regeneration unit catalyst outlet port and each riser reactor unit catalyst inlet port is in fluid communication with one of said outlet ports of the manifold;
a hydrocarbon separation unit having a gas inlet port in fluid communication with the gas-catalyst separation unit gas outlet ports, wherein the hydrocarbon separation unit separates ethylene and propylene from the hydrocarbon gas; and
at least one heat exchanger disposed between the gas-catalyst separation unit of a preceding reactor unit and a successive reactor unit for changing the temperature of the catalyst from the preceding reactor unit before directing the catalyst to the successive reactor unit, said at least one heat exchanger having an inlet port in fluid communication with the gas-catalyst separation unit catalyst outlet port of the preceding reactor unit and an outlet port in fluid communication with the successive reactor unit catalyst inlet port.

3. The apparatus of claim 2 wherein each riser reactor unit includes a plurality of sections and a plurality of catalyst inlet ports, wherein each catalyst inlet port enters a different section of the riser reactor unit and wherein the catalyst regeneration unit catalyst outlet port is in fluid communication with the plurality of riser reactor unit catalyst inlet ports.

* * * * *